United States Patent
Lee et al.

(10) Patent No.: US 9,695,256 B2
(45) Date of Patent: *Jul. 4, 2017

(54) MODIFIED CONJUGATED DIENE-BASED POLYMER, PREPARATION METHOD THEREFOR, AND RUBBER COMPOSITION COMPRISING SAME

(71) Applicant: LG Chem, Ltd., Seoul (KR)

(72) Inventors: Sangmi Lee, Daejeon (KR); Noma Kim, Daejeon (KR); Romi Lee, Daejeon (KR); Jinyoung Kim, Daejeon (KR); Youkreol Na, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/913,251

(22) PCT Filed: Oct. 17, 2014

(86) PCT No.: PCT/KR2014/009801
§ 371 (c)(1),
(2) Date: Feb. 19, 2016

(87) PCT Pub. No.: WO2015/057021
PCT Pub. Date: Apr. 23, 2015

(65) Prior Publication Data
US 2016/0208023 A1 Jul. 21, 2016

(30) Foreign Application Priority Data

Oct. 17, 2013 (KR) .................. 10-2013-0123915
Oct. 17, 2014 (KR) .................. 10-2014-0140852

(51) Int. Cl.
| | | |
|---|---|---|
| C08F 8/42 | (2006.01) |
| C08K 3/36 | (2006.01) |
| C07F 7/18 | (2006.01) |
| B60C 1/00 | (2006.01) |
| C08C 19/22 | (2006.01) |
| C08C 19/25 | (2006.01) |
| C08C 19/44 | (2006.01) |
| C08F 236/10 | (2006.01) |
| C08L 15/00 | (2006.01) |

(52) U.S. Cl.
CPC .............. *C08F 8/42* (2013.01); *B60C 1/00* (2013.01); *B60C 1/0016* (2013.04); *C07F 7/1836* (2013.01); *C08C 19/22* (2013.01); *C08C 19/25* (2013.01); *C08C 19/44* (2013.01); *C08F 236/10* (2013.01); *C08K 3/36* (2013.01); *C08L 15/00* (2013.01)

(58) Field of Classification Search
CPC ........ C08C 19/22; C08C 19/25; C07F 7/0812
USPC ................................................. 525/342, 375
See application file for complete search history.

(56) References Cited

U.S. PATENT DOCUMENTS

2008/0015309 A1 1/2008 Ozawa et al.
2012/0059112 A1* 3/2012 Luo .................. B60C 1/0016
  524/572
2012/0190771 A1 7/2012 Ito et al.
2012/0252966 A1 10/2012 Ito
2013/0023623 A1 1/2013 Nakamura et al.
2014/0114014 A1 4/2014 Tokimune et al.
2014/0243476 A1 8/2014 Lee et al.
2015/0005440 A1* 1/2015 Fujii .................... C08F 236/06
  524/547
2016/0177011 A1 6/2016 Kim et al.
2016/0208024 A1 7/2016 Kim et al.
2016/0230230 A1 8/2016 Ogier-Denis et al.

FOREIGN PATENT DOCUMENTS

| | | | |
|---|---|---|---|
| CN | 1599758 A | 3/2005 |
| CN | 101160353 A | 4/2008 |
| CN | 101268136 A | 9/2008 |
| CN | 102781968 A | 11/2012 |
| EP | 1854839 | * | 11/2007 |
| EP | 1854839 A1 | 11/2007 |
| EP | 1925636 B1 | 9/2011 |
| JP | H10280275 A | 10/1998 |
| JP | 2011-121906 | * | 6/2011 |
| JP | 2011-121906 A | 6/2011 |
| JP | 2013108035 A | 6/2013 |
| JP | 2013108043 A | 6/2013 |
| JP | 2013119558 A | 6/2013 |
| JP | 2013-133387 A | 7/2013 |
| JP | 2013-139491 A | 7/2013 |
| JP | 2013163748 A | 8/2013 |
| JP | 2016530376 A | 9/2016 |
| JP | 2016531554 A | 10/2016 |
| KR | 2007-0117626 A | 12/2007 |
| KR | 2008-0044880 A | 5/2008 |
| KR | 2013-0090810 A | 8/2013 |
| KR | 2013-0090811 A | 8/2013 |
| PA | 2016525626 A | 8/2016 |
| WO | 2013018424 A1 | 2/2013 |
| WO | 2013119006 A1 | 8/2013 |
| WO | 2016085102 A1 | 6/2016 |
| WO | 2016085143 A1 | 6/2016 |
| WO | 2016089035 A1 | 6/2016 |

OTHER PUBLICATIONS

Translation of JP 2011-121906 (2011).*
International Search Report for Application No. PCT/KR2014/009801 dated Jan. 5, 2015.
Search Report from European Application No. 14853983.6, dated Jul. 21, 2016.
Search Report from Chinese Office Action dated Nov. 1, 2016.

* cited by examiner

*Primary Examiner* — Robert C Boyle
(74) *Attorney, Agent, or Firm* — Lerner, David, Littenberg, Krumholz & Mentlik, LLP

(57) ABSTRACT

Disclosed is a method of preparing a modified conjugated diene-based polymer, including (a) polymerizing a conjugated diene monomer, or a conjugated diene monomer and an aromatic vinyl monomer, using the compound represented by Chemical Formula 1 in the presence of a solvent, thus obtaining an active polymer having a metal end, and (b) modifying the active polymer with the compound represented by Chemical Formula 2.

19 Claims, No Drawings

MODIFIED CONJUGATED DIENE-BASED POLYMER, PREPARATION METHOD THEREFOR, AND RUBBER COMPOSITION COMPRISING SAME

CROSS-REFERENCE TO RELATED APPLICATION

The present application is a national phase entry under 35 U.S.C. §371 of International Application No. PCT/KR2014/009801, filed Oct. 17, 2014, which claims priority from Korean Patent Application No. 10-2013-0123915, filed Oct. 17, 2013 and Korean Patent Application No. 10-2014-0140852, filed Oct. 17, 2014, all of which are incorporated herein by reference.

TECHNICAL FIELD

The present invention relates to a method of preparing a modified conjugated diene-based polymer. More particularly, the present invention relates to a method of preparing a modified conjugated diene-based polymer having superior heat build-up, tensile strength, wear resistance, and wet skid resistance, a modified conjugated diene-based polymer prepared thereby, and a rubber composition including the modified conjugated diene-based polymer.

BACKGROUND ART

With the recent trends in the vehicle industry, there is always the need for increased durability, stability and fuel economy, and continuous efforts to meet such needs have been made.

In particular, many attempts have been made to enhance the properties of rubber, which is the material for vehicle tires, especially tire treads, which are in contact with roads. The rubber composition for vehicle tires includes a conjugated diene-based polymer such as polybutadiene or a butadiene-styrene copolymer. To improve the performance of vehicle tires, research is currently ongoing into mixing a conjugated diene-based rubber composition with various enhancers.

The present inventors have proposed the present invention to develop, as a material for a tire tread, rubber having superior heat build-up, tensile strength, wear resistance, and wet skid resistance.

DISCLOSURE

Technical Problem

An object of the present invention is to provide a modified conjugated diene-based polymer having superior heat build-up, tensile strength, wear resistance, and wet skid resistance, and a method of preparing the same.

Another object of the present invention is to provide a modified conjugated diene-based polymer rubber composition including the modified conjugated diene-based polymer.

Still another object of the present invention is to provide a modifier for use in preparing the modified conjugated diene-based polymer.

Yet another object of the present invention is to provide a tire including the rubber composition.

Technical Solution

In order to accomplish the above objects, an aspect of the present invention provides a method of preparing a modified conjugated diene-based polymer, comprising: (a) polymerizing a conjugated diene monomer, or a conjugated diene monomer and an aromatic vinyl monomer, using the compound represented by Chemical Formula 1 below in the presence of a solvent, thus obtaining an active polymer having a metal end; and (b) modifying the active polymer with the compound represented by Chemical Formula 2 below.

[Chemical Formula 1]

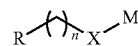

In Chemical Formula 1, R is a nitrogen-containing group, X is a hydrocarbon obtained by polymerization of the conjugated diene monomer or the aromatic vinyl monomer, n is an integer of 1~10, and M is an alkali metal.

[Chemical Formula 2]

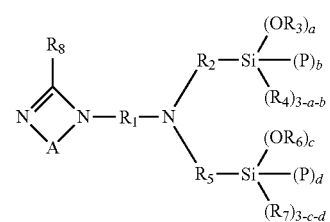

In Chemical Formula 2, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

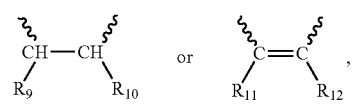

wherein $R_9$, $R_{10}$, $R_{11}$, and $R_{12}$ are each independently hydrogen or a C1-C10 alkyl group.

Another aspect of the present invention provides a modified conjugated diene-based polymer prepared by the above method, as represented by Chemical Formula 7 below.

[Chemical Formula 7]

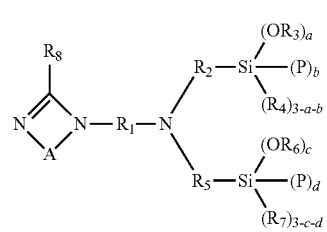

In Chemical Formula 7, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

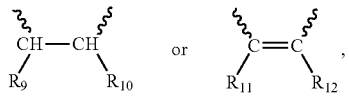

wherein $R_9$, $R_{10}$, $R_{11}$, and $R_{12}$ are each independently hydrogen or a C1-C10 alkyl group.

Still another aspect of the present invention provides a modified conjugated diene-based polymer rubber composition, comprising 100 parts by weight of the modified conjugated diene-based polymer and 0.1 to 200 parts by weight of an inorganic filler.

Yet another aspect of the present invention provides a modifier comprising the compound represented by Chemical Formula 2 below.

[Chemical Formula 2]

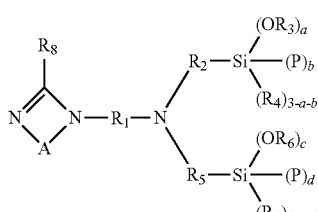

In Chemical Formula 2, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

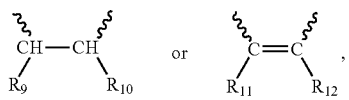

wherein $R_9$, $R_{10}$, $R_{11}$, and $R_{12}$ are each independently hydrogen or a C1-C10 alkyl group.

Still yet another aspect of the present invention provides a tire or tire tread using the modified conjugated diene-based polymer rubber composition.

Advantageous Effects

According to the present invention, a modified conjugated diene-based polymer having superior heat build-up, tensile strength, wear resistance, and wet skid resistance can be prepared, and can be used for a rubber composition for a tire.

BEST MODE

Hereinafter, a detailed description will be given of the present invention.

An aspect of the present invention addresses a method of preparing a modified conjugated diene-based polymer, comprising: (a) polymerizing a conjugated diene monomer, or a conjugated diene monomer and an aromatic vinyl monomer, using the compound represented by Chemical Formula 1 below, in the presence of a solvent, thus obtaining an active polymer having a metal end; and (b) modifying the active polymer with the compound represented by Chemical Formula 2 below.

[Chemical Formula 1]

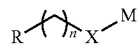

In Chemical Formula 1, R is a nitrogen-containing group, X is a hydrocarbon obtained by polymerization of the conjugated diene monomer or the aromatic vinyl monomer, n is an integer of 1~10, and M is an alkali metal.

[Chemical Formula 2]

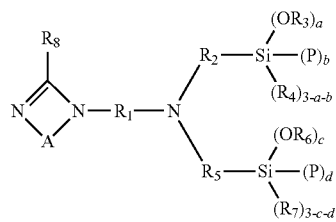

In Chemical Formula 2, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

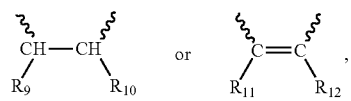

wherein $R_9$, $R_{10}$, $R_{11}$, and $R_{12}$ are each independently hydrogen or a C1-C10 alkyl group.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

The solvent is not particularly limited so long as it can be applied in the polymerization or copolymerization of the conjugated diene monomer, and may be exemplified by a hydrocarbon, or may include at least one selected from the group consisting of n-pentane, n-hexane, n-heptane, isooctane, cyclohexane, toluene, benzene, and xylene.

According to an embodiment of the present invention, the compound represented by Chemical Formula 1 may be used in an amount of 0.01 to 10 mmol, 0.05 to 5 mmol, 0.1 to 2 mmol, or 0.1 to 1 mmol, based on 100 g in total of the monomer. Given the above amount range of the compound represented by Chemical Formula 1, an optimal conjugated diene-based polymer for preparing a modified conjugated diene-based polymer may be prepared.

The molar ratio of the compound represented by Chemical Formula 1 and the compound represented by Chemical Formula 2 is, for example, 1:0.1 to 1:10, and preferably 1:0.3 to 1:2. Given the above molar ratio, the conjugated diene-based polymer may undergo a modification reaction to ensure optimal performance.

The active polymer having the metal end indicates a polymer comprising a polymer anion and a metal cation, which are linked with each other.

According to an embodiment of the present invention, in the method of preparing the modified conjugated diene-based polymer, polymerizing in (a) may be performed with the additional use of a polar additive. The reason why the polar additive is further added is that the reaction rate of the conjugated diene monomer with the aromatic vinyl monomer is controlled by the polar additive.

The polar additive may be an alkali, or may include ether, amine, or mixtures thereof, and may be specifically selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine. Preferably useful is ditetrahydrofurylpropane, triethylamine or tetramethylethylenediamine.

The polar additive may be used in an amount of 0.001 to 50 g, 0.001 to 10 g, 0.005 to 1 g, or 0.005 to 0.1 g, based on 100 g in total of the added monomer.

Also, the polar additive may be used in an amount of 0.001 to 10 g, 0.005 to 1 g, or 0.005 to 0.1 g, based on 1 mmol in total of the added compound, represented by Chemical Formula 1.

When the conjugated diene monomer and the aromatic vinyl monomer are copolymerized, it is easy to prepare a block copolymer due to the difference in the reaction rate therebetween. However, when the polar additive is added, the low reaction rate of the aromatic vinyl monomer may be increased to thus induce the microstructure of the corresponding copolymer, for example, a random copolymer.

In (a), the polymerizing may be exemplified by anionic polymerization. Specifically, polymerizing in (a) may be living anionic polymerization for forming an active end through a growth reaction by anions.

Also, polymerizing in (a) may be increasing-temperature polymerization or fixed-temperature polymerization.

Increasing-temperature polymerization is a polymerization process including adding an organic metal compound and then applying heat to increase the reaction temperature, and fixed-temperature polymerization is a polymerization process that takes place in such a way that heat is not applied after the addition of an organic metal compound.

Polymerizing in (a) may take place at a temperature ranging from −20 to 200° C., 0 to 150° C., or 10 to 120° C.

In (b), at least one, or two or three, selected from among the compounds represented by Chemical Formula 2 may be added.

Also, (b) may be performed at 0 to 90° C. for 1 min to 5 hr.

According to an embodiment of the present invention, the method of preparing the modified conjugated diene-based polymer may be carried out in a batch manner, or a continuous manner using at least one reactor.

The compound of Chemical Formula 2 may be represented by, for example, Chemical Formula 3 or Chemical Formula 4 below.

[Chemical Formula 3]

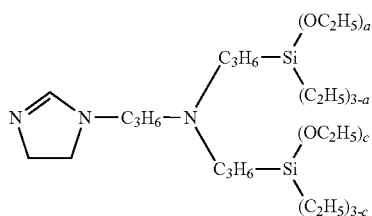

[Chemical Formula 4]

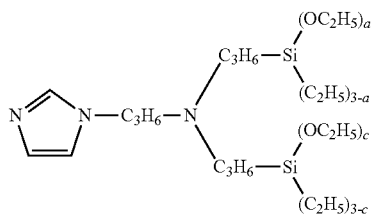

In Chemical Formulas 3 and 4, a and c are each independently 0, 1, or 2.

Also, the compound of Chemical Formula 2 may be represented by Chemical Formula 5 or Chemical Formula 6 below.

[Chemical Formula 5]

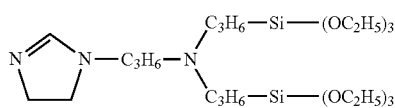

[Chemical Formula 6]

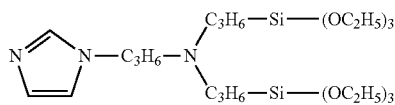

Another aspect of the present invention provides a modified conjugated diene-based polymer prepared by the method described above.

The modified conjugated diene-based polymer may be represented by Chemical Formula 7 below.

[Chemical Formula 7]

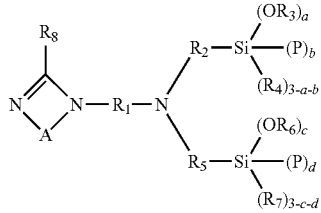

In Chemical Formula 7, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

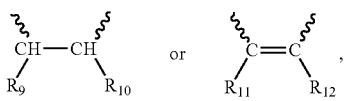

wherein $R_9$, $R_{10}$, $R_{11}$, and $R_{12}$ are each independently hydrogen or a C1-C10 alkyl group.

The modified conjugated diene-based polymer has a number average molecular weight (Mn) of 1,000 to 2,000,000 g/mol, preferably 10,000 to 1,000,000 g/mol, and more preferably 100,000 to 1,000,000 g/mol. Given the above Mn range of the modified conjugated diene-based polymer, a modification reaction may be efficiently carried out, or good properties may result.

The modified conjugated diene-based polymer has a polydispersity index (Mw/Mn) of 0.5 to 10, preferably 0.5 to 5, and more preferably 1 to 4. Given the above Mw/Mn range of the modified conjugated diene-based polymer, mixing with inorganic particles may be carried out efficiently to thereby improve the properties thereof and ensure very good processability.

The modified conjugated diene-based polymer has a vinyl content of 10 wt % or more, preferably 15 wt % or more, and more preferably 20 to 70 wt %.

The vinyl content indicates the amount of a monomer having a vinyl group, or the amount of not 1,4- but 1,2-added conjugated diene monomer based on 100 wt % of the conjugated diene monomer.

Given the above vinyl content range of the modified conjugated diene-based polymer, the glass transition temperature of the polymer may be raised, and thus, when such a polymer is applied to tires, the properties required of tires, such as running resistance and braking force, may be satisfactory and fuel economy may be improved.

The conjugated diene-based polymer chain represented by P in Chemical Formula 7 may be derived from a homopolymer of a conjugated diene monomer or a copolymer of a conjugated diene monomer and an aromatic vinyl monomer.

Specifically, the conjugated diene-based polymer chain may be formed as follows: a conjugated diene monomer or a conjugated diene monomer and an aromatic vinyl monomer may be polymerized in a batch or continuous manner using a hydrocarbon solvent in the presence of an organic alkali metal compound, thus obtaining a homopolymer or a copolymer having an alkali metal end, which is then reacted with a silyl group substituted with at least one alkoxy group.

As such, the conjugated diene-based polymer chain may be a polymer chain comprising 0.0001 to 50 wt %, 10 to 40 wt %, or 20 to 40 wt % of the aromatic vinyl monomer, based on 100 wt % in total of the conjugated diene monomer, or the conjugated diene monomer and the aromatic vinyl monomer.

The polymer chain comprising the conjugated diene monomer and the aromatic vinyl monomer may be, for example, a random polymer chain.

As such, the conjugated diene monomer and the aromatic vinyl monomer are described as above.

The modified conjugated diene-based polymer has a Mooney viscosity of 40 or more, preferably 40 to 100, and more preferably 45 to 90. Given the above Mooney viscosity range, it is possible to prepare a modified conjugated diene-based polymer having excellent processability, compatibility, heat build-up, tensile strength, wear resistance, fuel economy, and wet skid resistance.

According to an embodiment of the present invention, the modified conjugated diene-based polymer may be represented by Chemical Formula 8 or Chemical Formula 9 below.

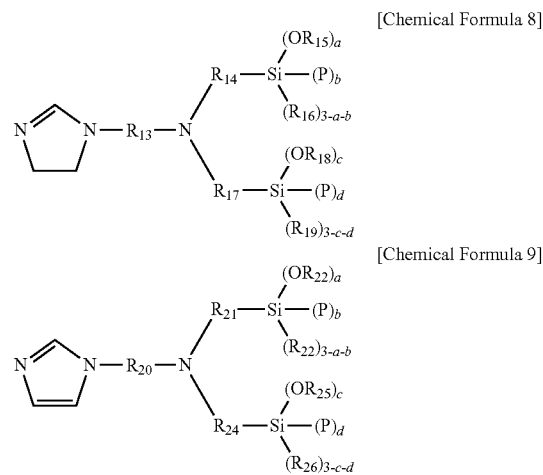

[Chemical Formula 8]

[Chemical Formula 9]

In Chemical Formulas 8 and 9, $R_{15}$, $R_{16}$, $R_{18}$, $R_{19}$, $R_{22}$, $R_{23}$, $R_{25}$, and $R_{26}$ are each independently a C1-C5 alkyl group, $R_{13}$, $R_{14}$, $R_{17}$, $R_{20}$, $R_{21}$, and $R_{24}$ are each independently a C1-C5 alkylene group, P is a conjugated diene-based polymer chain, a and c are each independently 0, 1, or 2, b and d are each independently 1, 2, or 3, and a+b and c+d are each independently 1, 2, or 3.

Also, the modified conjugated diene-based polymer may be represented by Chemical Formula 10 or Chemical Formula 11 below.

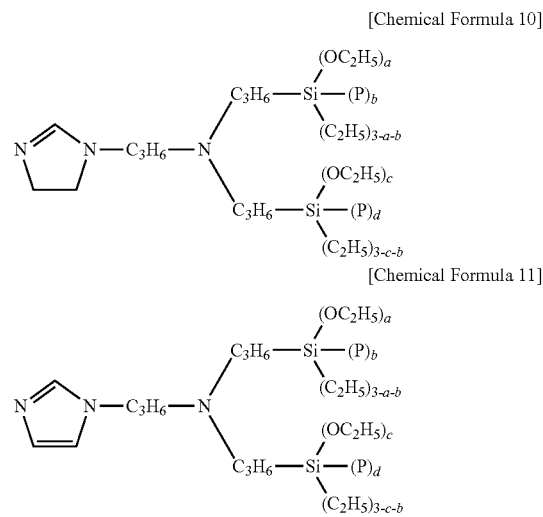

[Chemical Formula 10]

[Chemical Formula 11]

In Chemical Formulas 10 and 11, P is a conjugated diene-based polymer chain, a and c are each independently 0, 1, or 2, b and d are each independently 1, 2, or 3, and a+b and c+d are each independently 1, 2, or 3.

Specifically, the modified conjugated diene-based polymer may be represented by Chemical Formula 12 or Chemical Formula 13 below.

[Chemical Formula 12]

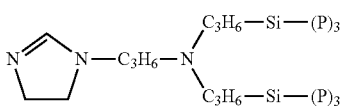

[Chemical Formula 13]

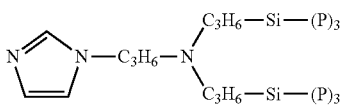

In Chemical Formulas 12 and 13, P is a conjugated diene-based polymer chain.

The modified conjugated diene-based polymer may exhibit viscoelastic properties. When measured at 10 Hz using DMA after mixing with silica, Tan δ at 0° C. may be in the range of 0.4 to 1, or 0.5 to 1. Given the above Tan δ range, skid resistance or wet resistance may be significantly improved.

Also, Tan δ at 60° C. may be in the range of 0.3 to 0.2, or 0.15 to 0.1. Given the above Tan δ range, rolling resistance or rotational resistance (RR) may be significantly improved.

Still another aspect of the present invention addresses a modified conjugated diene-based polymer rubber composition, comprising 100 parts by weight of the modified conjugated diene-based polymer and 0.1 to 200 parts by weight of an inorganic filler.

The amount of the inorganic filler may be 10 to 150 parts by weight, or 50 to 100 parts by weight.

The inorganic filler may include at least one selected from the group consisting of a silica-based filler, carbon black, and mixtures thereof. When the inorganic filler is a silica-based filler, dispersibility is greatly improved and silica particles are linked with the end of the modified conjugated diene-based polymer of the invention, thus significantly decreasing hysteresis loss.

The modified conjugated diene-based polymer rubber composition may further comprise an additional conjugated diene-based polymer.

The additional conjugated diene-based polymer may include SBR (styrene-butadiene rubber), BR (butadiene rubber), natural rubber, or mixtures thereof. SBR may be exemplified by SSBR (solution styrene-butadiene rubber).

When the additional conjugated diene-based polymer is further added, the modified conjugated diene-based polymer rubber composition may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, provided that the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

In addition, the modified conjugated diene-based polymer rubber composition may further comprise 1 to 100 parts by weight of oil. The oil may be exemplified by mineral oil or a softener.

The oil may be used in an amount of, for example, 10 to 100 parts by weight, or 20 to 80 parts by weight, based on 100 parts by weight of the conjugated diene-based polymer. Given the above oil amount range, desired properties may be exhibited, and the rubber composition is appropriately softened, thus improving processability.

Yet another aspect of the present invention addresses a modifier comprising the compound represented by Chemical Formula 2 below.

[Chemical Formula 2]

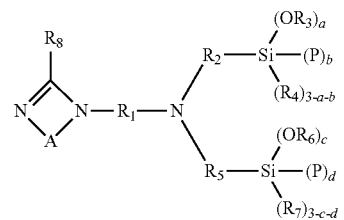

In Chemical Formula 2, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

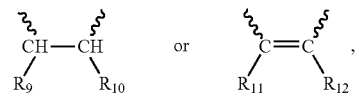

wherein $R_9$, $R_{10}$, $R_{11}$, and $R_{12}$ are each independently hydrogen or a C1-C10 alkyl group.

The compound of Chemical Formula 2 may be represented by, for example, Chemical Formula 3 or Chemical Formula 4 below.

[Chemical Formula 3]

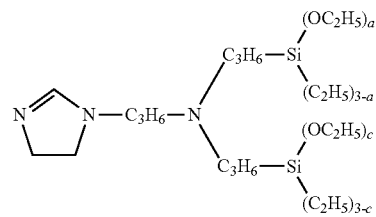

-continued

[Chemical Formula 4]

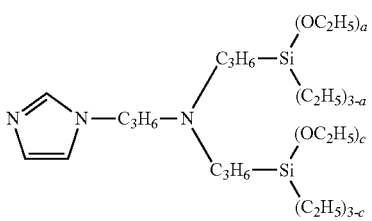

In Chemical Formulas 3 and 4, a and c are each independently 0, 1, or 2.

Also, the compound of Chemical Formula 2 may be represented by Chemical Formula 5 or Chemical Formula 6 below.

[Chemical Formula 5]

[Chemical Formula 6]

Still yet another aspect of the present invention addresses a tire or tire tread using the modified conjugated diene-based polymer rubber composition as above.

The tire or tire tread is manufactured using the rubber composition comprising the modified conjugated diene-based polymer, which has superior compatibility with the inorganic filler and improved processability, and thus manifests excellent tensile strength, wear resistance, and wet skid resistance, and reduced rolling resistance.

A better understanding of the present invention may be obtained via the following examples. However, embodiments of the present invention may be changed in various forms, and are not construed as limiting the scope of the present invention. The embodiments of the present invention are provided to fully describe the present invention to those having ordinary knowledge in the art to which the present invention pertains.

MODE FOR INVENTION

Example 1: Preparation of Conjugated Diene-Based Polymer

In a 20 L autoclave reactor, 270 g of styrene, 710 g of 1,3-butadiene, 5000 g of n-hexane, and 0.9 g of 2,2-bis(2-oxoranyl)propane as a polar additive were placed, and then the temperature inside the reactor was increased to 40° C. When the temperature inside the reactor reached 40° C., 4.3 mmol of 3-(dimethylamino)-1-propyllithium-(isoprene)n was placed in the reactor, followed by an adiabatic heating reaction. About 20 min after the adiabatic heating reaction, 20 g of 1,3-butadiene was added. After 5 min, 4.3 mmol of N,N-bis(triethoxysilylpropyl)aminopropyl-1-imidazole was added, and the reaction was carried out for 15 min. Then, the polymerization reaction was stopped using ethanol, and 45 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 2: Preparation of Conjugated Diene-Based Polymer

Three reactors were prepared. Among them, the first and the second reactor were used as polymerization reactors, and the third reactor was used as a modification reactor.

Styrene, 1,3-butadiene, and n-hexane, without impurities such as water, were mixed at rates of 1.788 kg/h, 4.477 kg/h, and 4.176 kg/h, respectively, before being placed in the reactors. The resulting mixed solution was continuously fed into the first reactor. Subsequently, 2,2-bis(2-oxoranyl)propane as a polar additive and 3-(dimethylamino)-1-propyllithium-(isoprene)n were fed at rates of 4.1 g/h and 22.4 mmol/h, respectively, into the first reactor, and the temperature inside the reactor was adjusted to 70° C.

The polymer output from the first reactor was continuously fed into the upper portion of the second reactor, and a polymerization reaction was carried out while the temperature was maintained at 85° C. The polymer output from the second reactor was continuously fed into the upper portion of the third reactor, N,N-bis(triethoxysilylpropyl)aminopropyl-1-imidazole was continuously fed at a rate of 10.9 mmol/h, and a modification reaction was carried out. To the polymer output from the third reactor, a mixed solution of isopropylalcohol and an antioxidant (Wingstay-K) at 8:2 was added at a rate of 32.5 g/h to stop the polymerization reaction, yielding a polymer.

100 parts by weight of the polymer thus obtained was mixed with 25 phr of TDAE oil (a distilled aromatic extract having a glass transition temperature of about −44 to about −50° C.), placed in water warmed with steam, stirred to remove the solvent, and then roll dried to remove the remaining solvent and water, yielding a modified conjugated diene-based polymer. The results of analysis of the modified conjugated diene-based polymer thus obtained are shown in Table 2 below.

Comparative Example 1: Preparation of Conjugated Diene-Based Polymer

A modified conjugated diene-based polymer was prepared in the same manner as in Example 1, with the exception that 4 mmol of n-butyllithium was used as the initiator, instead of 3-(dimethylamino)-1-propyllithium-(isoprene)n. The results of analysis of the modified conjugated diene-based polymer thus obtained are shown in Table 1 below.

Comparative Example 2: Preparation of Conjugated Diene-Based Polymer

A modified conjugated diene-based polymer was prepared in the same manner as in Example 1, with the exception that 4 mmol of n-butyllithium was used as the initiator, instead of 3-(dimethylamino)-1-propyllithium-(isoprene)n, and 1.2 mmol of dimethylchlorosilane was used as the coupling agent, instead of N,N-bis(triethoxysilylpropyl)aminopropyl- 1-imidazole. The results of analysis of the modified conjugated diene-based polymer thus obtained are shown in Table 1 below.

Comparative Example 3: Preparation of Conjugated Diene-Based Polymer

The results of analysis of a commercially available non-modified conjugated diene-based polymer (5025-2HM grade, made by LANXESS Deutschland GmbH) are shown in Table 1 below. For reference, in the non-modified conjugated diene-based polymer (TUFDENE™ 3835), RAE oil was used, in lieu of TDAE oil, which was used in Example 1.

Comparative Example 4: Preparation of Conjugated Diene-Based Polymer

A modified conjugated diene-based polymer was prepared in the same manner as in Example 2, with the exception that n-butyllithium was added at 39.57 mmol/h as the initiator, instead of 3-(dimethylamino)-1-propyllithium-(isoprene)n. The results of analysis of the modified conjugated diene-based polymer thus obtained are shown in Table 2 below.

Comparative Example 5: Preparation of Conjugated Diene-Based Polymer

The results of analysis of a commercially available non-modified conjugated diene-based polymer (5025-2HM grade, made by LANXESS Deutschland GmbH) are shown in Table 2 below.

For reference, in the non-modified conjugated diene-based polymer (TUFDENE™ 3835), RAE oil was used, in lieu of TDAE oil, which was used in Example 1.

The conjugated diene-based polymers prepared in Examples 1 and 2 and Comparative Examples 1 to 5 were analyzed through the following methods.

a) Mooney viscosity: Two samples having a weight of 15 g or more were preheated for 1 min and then measured at 100° C. for 4 min using an MV-2000, made by ALPHA Technologies.

b) Styrene monomer (SM) and Vinyl content: Measurement was conducted using NMR.

c) Weight average molecular weight (Mw), Number average molecular weight (Mn), and Polydispersity Index (PDI): Measurement was conducted via GPC at 40° C. For this, a column was composed of a combination of two PLgel Olexis columns and one PLgel mixed-C column, made by Polymer Laboratories, and all newly replaced columns were mixed bed type columns. Also, polystyrene (PS) was a GPC standard material for calculation of the molecular weight.

TABLE 1

|  |  | Ex. 1 | C. Ex. 1 | C. Ex. 2 | C. Ex. 3 |
|---|---|---|---|---|---|
| Sample |  | A | B | C | D |
| Initiator (mmol) | n-Butyllithium | — | 4 | 4 | — |
|  | a* | 4.3 | — | — | — |
| Polar additive (g) |  | 0.9 | 0.9 | 0.9 | — |
| Modifier (mmol) | b* | 4.3 | 4.3 | — | — |
| Coupling agent | c* | — | — | 1.2 | — |
| Mooney viscosity (MV) |  | 95 | 88 | 64 | 61 |
| TDAE oil (phr) |  | — | — | — | RAE 37.5 |
| NMR (%) | SM | 27 | 27 | 27 | 25 |
|  | Vinyl | 43 | 41 | 43 | 49 |
| GPC (×10⁴) | Mn | 41 | 39 | 31 | 39 |
|  | Mw | 59 | 55 | 50 | 69 |
|  | PDI | 1.4 | 1.4 | 1.2 | 1.8 | a*: 3-(Dimethylamino)-1-propyllithium-(isoprene)n
b*: N,N-Bis(triethoxysilylpropyl)aminopropyl-1-imidazole
c*: Dimethyldichlorosilane
D: 5025-2HM grade, made by LANXESS Deutschland GmbH

TABLE 2

|  |  | Ex. 2 | C. Ex. 4 | C. Ex. 5 |
|---|---|---|---|---|
| Sample |  | E | F | D |
| Initiator (mmol) | n-Butyllithium | — | 39.57 | — |
|  | a* | 22.4 | — | — |
| Polar additive (g/h) |  | 4.1 | 4.1 | — |
| Modifier (mmol) | b* | 10.9 | 10.9 | — |
| Mooney viscosity (MV) |  | 86 | 75 | 61 |
| TDAE oil (phr) |  | 25 | 25 | RAE 37.5 |
| NMR (%) | SM | 27 | 27 | 25 |
|  | Vinyl | 43 | 43 | 49 |
| GPC (×10⁴) | Mn | 49 | 47 | 39 |
|  | Mw | 119 | 144 | 69 |
|  | PDI | 2.4 | 3.1 | 1.8 | a*: 3-(Dimethylamino)-1-propyllithium-(isoprene)n
b*: N,N-Bis(triethoxysilylpropyl)aminopropyl-1-imidazole
D: 5025-2HM grade, made by LANXESS Deutschland GmbH Preparation of Conjugated Diene-Based Polymer Rubber Composition The conjugated diene-based polymer rubber compositions of Preparation Examples 1 and 2 and Comparative Preparation Examples 1 to 5 were prepared using, as raw rubber, samples A, B, C, D, E, F and D shown in Tables 1 and 2, under the mixing conditions of Table 3 below. The unit of material in Table 3 is phr, based on 100 parts by weight of rubber.

Specifically, the conjugated diene-based polymer rubber composition was kneaded through primary kneading and secondary kneading. Upon primary kneading, raw rubber (conjugated diene-based polymer), a filler, an organosilane coupling agent, oil, zinc oxide, a stearic acid antioxidant, an anti-aging agent, wax and an accelerator were kneaded using a Banbury mixer provided with a temperature controller. For this, the temperature of the kneader was controlled, and a first mixture was obtained at a discharge temperature of 145 to 155° C. Upon secondary kneading, the first mixture was cooled to room temperature, after which rubber, sulfur and a vulcanization accelerator were placed in the kneader, followed by mixing at 100° C. or less, thus obtaining a second mixture. Finally, curing was performed at 100° C. for 20 min, yielding the conjugated diene-based polymer rubber compositions of Preparation Examples 1 and 2 using, as raw rubber, the polymers of Examples 1 and 2, and of Comparative Preparation Examples 1 to 5 using the polymers of Comparative Examples 1 to 5 as raw rubber.

TABLE 3

|  | Material | Amount (unit: phr) |
|---|---|---|
| Primary kneading | Rubber | 137.5 |
|  | Silica | 70.0 |
|  | Coupling agent | 11.2 |
|  | Oil | — |
|  | Zinc oxide | 3.0 |
|  | Stearic acid | 2.0 |
|  | Antioxidant | 2.0 |
|  | Anti-aging agent | 2.0 |
|  | Wax | 1.0 |

TABLE 3-continued

| | Material | Amount (unit: phr) |
|---|---|---|
| Secondary kneading | Rubber accelerator | 1.75 |
| | Sulfur | 1.5 |
| | Vulcanization accelerator | 2.0 |
| | Total weight | 234.0 |

The properties of the prepared rubber compositions were measured through the following methods.

1) Tensile Testing

According to a tensile testing method of ASTM 412, the tensile strength upon cutting a test sample and tensile stress (300% modulus) at 300% elongation were measured. To this end, a Universal Test Machine 4204 made by Instron was used, and the tensile strength, modulus, and elongation were measured at a tensile rate of 50 cm/min at room temperature.

2) Viscoelasticity

A dynamic mechanical analyzer made by TA was used. When undergoing deformation under conditions of a frequency of 10 Hz in a distortion mode and a measurement temperature (−60 to 60° C.), the Tan δ of each sample was measured. The Payne effect was represented by the difference between the minimum and the maximum in the deformation range of 0.28 to 40%. The lower the Payne effect, the higher the dispersibility of the filler such as silica. When Tan δ at a low temperature of 0° C. was increased, wet skid resistance became superior, and when Tan δ at a high temperature of 60° C. was decreased, low hysteresis loss and low rolling resistance of tires, namely, improved fuel economy, resulted. Tables 4 and 5 below show the properties of the vulcanized rubber.

TABLE 4

| | Prep. Ex. 1 | C. Prep. Ex. 1 | C. Prep. Ex. 2 | C. Prep. Ex. 3 |
|---|---|---|---|---|
| Sample | A | B | C | D |
| 300% Modulus (Kgf/cm$^2$) | 141 | 132 | 104 | 98 |
| Tensile strength (Kgf/cm$^2$) | 215 | 213 | 168 | 161 |
| Tanδ at 0° C. | 1.008 | 0.967 | 0.542 | 0.647 |
| Tanδ at 60° C. | 0.091 | 0.101 | 0.115 | 0.133 |
| ΔG' at 60° C. (Payne Effect) | 0.28 | 0.29 | 0.74 | 0.56 |

TABLE 5

| | Prep. Ex. 2 | C. Prep. Ex. 4 | C. Prep. Ex. 5 |
|---|---|---|---|
| Sample | E | F | D |
| 300% Modulus (Kgf/cm$^2$) | 135 | 122 | 98 |
| Tensile strength (Kgf/cm$^2$) | 203 | 193 | 161 |
| Tanδ at 0° C. | 0.965 | 0.915 | 0.647 |
| Tanδ at 60° C. | 0.101 | 0.108 | 0.133 |
| ΔG' at 60° C. (Payne Effect) | 0.29 | 0.29 | 0.56 |

As is apparent from the results of Tables 4 and 5, the modified conjugated diene-based polymer rubber compositions of Preparation Examples 1 and 2 according to the present invention were significantly improved in 300% modulus (tensile stress) and tensile strength, compared to Comparative Preparation Examples 3 and 5, and also exhibited low Tan δ at 60° C. Thus, when manufacturing a tire using the modified conjugated diene-based polymer rubber composition of the invention, rolling resistance was decreased, whereby good fuel efficiency resulted.

Also, the conjugated diene-based polymer rubber compositions of Preparation Examples 1 and 2 according to the present invention exhibited high Tan δ at 0° C., compared to Comparative Preparation Examples 1 to 5. Thus, when a tire was manufactured using the modified conjugated diene-based polymer rubber composition of the invention, high wet skid resistance resulted.

Also, the modified conjugated diene-based polymer rubber compositions of Preparation Examples 1 and 2 according to the present invention exhibited low ΔG' at 60° C., compared to Comparative Preparation Examples 1 and 2, thus improving silica dispersibility.

The invention claimed is:

1. A method of preparing a modified conjugated diene-based polymer, comprising:
   (a) polymerizing a conjugated diene monomer, or a conjugated diene monomer and an aromatic vinyl monomer, using a compound represented by Chemical Formula 1 below, in presence of a solvent, thus obtaining an active polymer having a metal end; and
   (b) modifying the active polymer with any one of compounds represented by Chemical Formula 3 to 6 below:

[Chemical Formula 1]

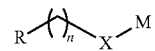

in Chemical Formula 1, R is a nitrogen-containing group, X is a hydrocarbon obtained by polymerization of the conjugated diene monomer or the aromatic vinyl monomer, n is an integer of 1~10, and M is an alkali metal; and

[Chemical Formula 3]

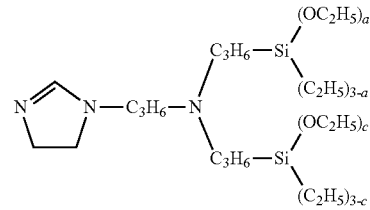

[Chemical Formula 4]

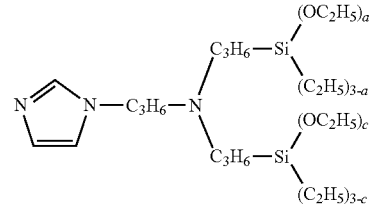

in Chemical Formulas 3 and 4, a and c are each independently 1, or 2,

[Chemical Formula 5]

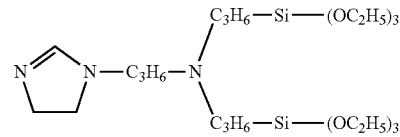

[Chemical Formula 6]

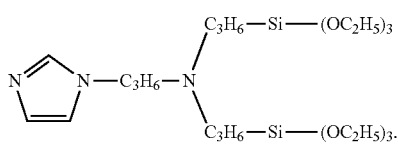

2. The method of claim 1, wherein the compound represented by Chemical Formula 1 is used in an amount of 0.01 to 10 mmol based on 100 g in total of the monomer.

3. The method of claim 1, wherein a molar ratio of the compound represented by Chemical Formula 1 and any one of the compounds represented by Chemical Formula 3 to 6 is 1:0.1 to 1:10.

4. The method of claim 1, wherein (a) is performed with additional use of a polar additive.

5. The method of claim 4, wherein the polar additive is added in an amount of 0.001 to 10 g based on 1 mmol in total of the compound represented by Chemical Formula 1.

6. A modified conjugated diene-based polymer represented by Chemical Formula 7 below:

[Chemical Formula 7]

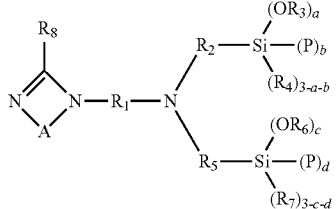

in Chemical Formula 7, $R_1$, $R_2$, and $R_5$ are each independently a C1-C10 alkylene group, $R_3$, $R_4$, $R_6$ and $R_7$ are each independently a C1-C10 alkyl group, $R_8$ is hydrogen or a C1-C10 alkyl group, P is a conjugated diene-based polymer chain, a and c are each independently 0, 1, or 2, b and d are each independently 1, 2, or 3, a+b and c+d are each independently 1, 2, or 3, and A is

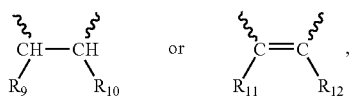

wherein $R_9$, $R_{10}$, $R_{11}$, and $R_{12}$ are each independently hydrogen or a C1-C10 alkyl group.

7. The modified conjugated diene-based polymer of claim 6, wherein Chemical Formula 7 is represented by Chemical Formula 8 or Chemical Formula 9 below:

[Chemical Formula 8]

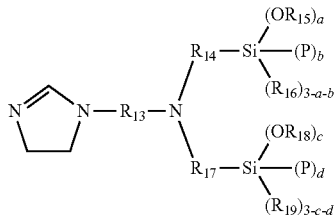

[Chemical Formula 9]

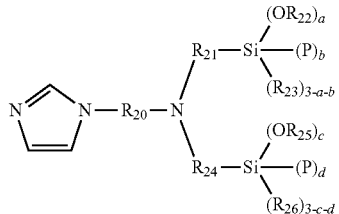

in Chemical Formulas 8 and 9, $R_{15}$, $R_{16}$, $R_{18}$, $R_{19}$, $R_{22}$, $R_{23}$, $R_{25}$, and $R_{26}$ are each independently a C1-C5 alkyl group, $R_{13}$, $R_{14}$, $R_{17}$, $R_{20}$, $R_{21}$, and $R_{24}$ are each independently a C1-C5 alkylene group, P is a conjugated diene-based polymer chain, a and c are each independently 0, 1, or 2, b and d are each independently 1, 2, or 3, and a+b and c+d are each independently 1, 2, or 3.

8. The modified conjugated diene-based polymer of claim 6, wherein Chemical Formula 7 is represented by Chemical Formula 10 or Chemical Formula 11 below:

[Chemical Formula 10]

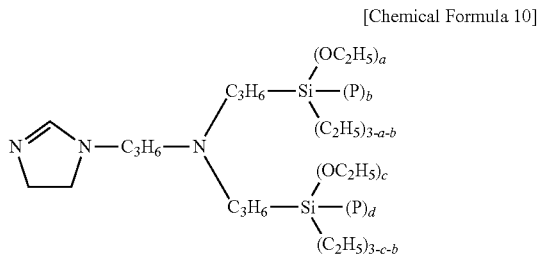

[Chemical Formula 11]

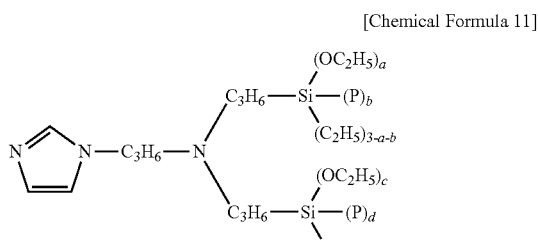

in Chemical Formulas 10 and 11, P is a conjugated diene-based polymer chain, a and c are each independently 0, 1, or 2, b and d are each independently 1, 2, or 3, and a+b and c+d are each independently 1, 2, or 3.

9. The modified conjugated diene-based polymer of claim 6, wherein Chemical Formula 7 is represented by Chemical Formula 12 or Chemical Formula 13 below:

[Chemical Formula 12]

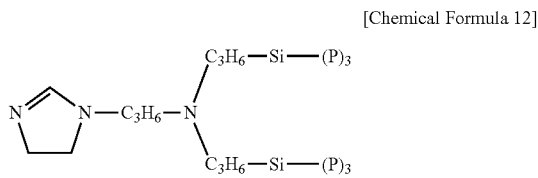

-continued

[Chemical Formula 13]

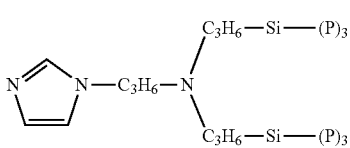

in Chemical Formulas 12 and 13, P is a conjugated diene-based polymer chain.

10. The modified conjugated diene-based polymer of claim 6, wherein the modified conjugated diene-based polymer has a number average molecular weight (Mn) of 1,000 to 2,000,000 g/mol.

11. The modified conjugated diene-based polymer of claim 6, wherein the modified conjugated diene-based polymer has a polydispersity index (Mw/Mn) of 0.5 to 10.

12. The modified conjugated diene-based polymer of claim 6, wherein the modified conjugated diene-based polymer has a vinyl content of 10 wt % or more.

13. The modified conjugated diene-based polymer of claim 6, wherein the conjugated diene-based polymer chain is derived from a homopolymer of a conjugated diene monomer or a copolymer of a conjugated diene monomer and an aromatic vinyl monomer.

14. The modified conjugated diene-based polymer of claim 6, wherein the modified conjugated diene-based polymer includes 0.0001 to 50 wt % of an aromatic vinyl monomer based on 100 wt % in total of the conjugated diene monomer and the aromatic vinyl monomer.

15. The modified conjugated diene-based polymer of claim 6, wherein the modified conjugated diene-based polymer has a Mooney viscosity of 40 or more.

16. A modified conjugated diene-based polymer rubber composition, comprising 100 parts by weight of the modified conjugated diene-based polymer of claim 6 and 0.1 to 200 parts by weight of an inorganic filler.

17. The modified conjugated diene-based polymer rubber composition of claim 16, wherein the inorganic filler comprises at least one selected from the group consisting of a silica-based filler, carbon black, and mixtures thereof.

18. A modifier comprising any one of compounds represented by Chemical Formulas 3 to 6 below:

[Chemical Formula 3]

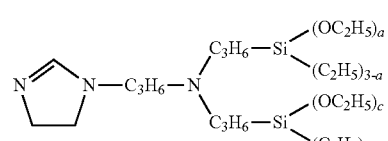

[Chemical Formula 4]

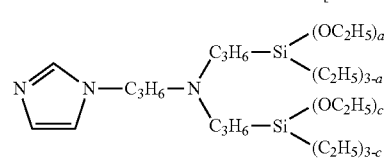

in Chemical Formulas 3 and 4, a and c are each independently 1, or 2,

[Chemical Formula 5]

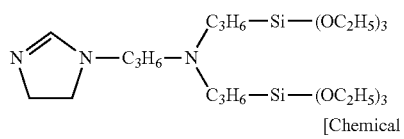

[Chemical Formula 6]

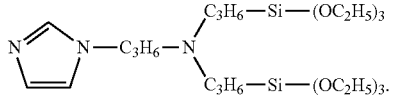

19. A tire or tire tread, comprising the modified conjugated diene-based polymer rubber composition of claim 16.

* * * * *